United States Patent
Ryan

[19]

[11] Patent Number: 5,811,303
[45] Date of Patent: Sep. 22, 1998

[54] QUANTITATIVE BUFFY COAT CONTROL COMPOSITION

[75] Inventor: Wayne L. Ryan, Omaha, Nebr.

[73] Assignee: Streck Laboratories, Inc., Omaha, Nebr.

[21] Appl. No.: 831,409

[22] Filed: Apr. 1, 1997

[51] Int. Cl.⁶ .................................................. G01N 31/00
[52] U.S. Cl. .................................. 436/16; 436/8; 436/63; 436/70; 436/166; 436/174; 252/408.1
[58] Field of Search .................... 436/8, 10, 15, 436/16, 18, 63, 66, 69, 70, 164, 166, 174; 435/2; 252/408.1

[56] References Cited

U.S. PATENT DOCUMENTS

| | | | |
|---|---|---|---|
| 3,873,467 | 3/1975 | Hunt | 436/10 |
| 4,007,396 | 2/1977 | Wisbey et al. | 313/500 |
| 4,027,660 | 6/1977 | Wardlaw et al. | 600/584 |
| 4,082,085 | 4/1978 | Wardlaw et al. | 600/309 |
| 4,091,659 | 5/1978 | Massey, III et al. | 73/61.63 |
| 4,137,755 | 2/1979 | Wardlaw et al. | 73/61.43 |
| 4,141,654 | 2/1979 | Wardlaw et al. | 356/243 |
| 4,156,570 | 5/1979 | Wardlaw | 356/36 |
| 4,159,896 | 7/1979 | Levine et al. | 436/177 |
| 4,181,609 | 1/1980 | Wardlaw et al. | 210/774 |
| 4,190,328 | 2/1980 | Levine et al. | 356/39 |
| 4,209,226 | 6/1980 | Wardlaw et al. | 359/388 |
| 4,259,012 | 3/1981 | Wardlaw | 356/39 |
| 4,264,470 | 4/1981 | Chastain, Jr. et al. | 436/10 |
| 4,299,726 | 11/1981 | Crews et al. | 436/10 |
| 4,331,862 | 5/1982 | Ryan | 377/29 |
| 4,358,394 | 11/1982 | Crews et al. | 436/10 |
| 4,390,632 | 6/1983 | Carter, II | 436/10 |
| 4,558,947 | 12/1985 | Wardlaw | 356/39 |
| 4,567,754 | 2/1986 | Wardlaw et al. | 73/61.43 |
| 4,594,165 | 6/1986 | Levine et al. | 210/767 |
| 4,683,579 | 7/1987 | Wardlaw | 377/11 |
| 4,695,553 | 9/1987 | Wardlaw et al. | 436/177 |
| 4,698,312 | 10/1987 | Wong et al. | 436/10 |
| 4,704,364 | 11/1987 | Carver et al. | 436/10 |
| 4,774,965 | 10/1988 | Rodriguez et al. | 128/771 |
| 4,777,139 | 10/1988 | Wong et al. | 436/18 |
| 4,779,976 | 10/1988 | Levine et al. | 356/39 |
| 5,262,327 | 11/1993 | Ryan | 436/10 |
| 5,270,208 | 12/1993 | Ryan | 436/10 |
| 5,270,209 | 12/1993 | Rigg et al. | 436/39 |
| 5,422,277 | 6/1995 | Connelly et al. | 436/10 |
| 5,516,695 | 5/1996 | Kim et al. | 436/17 |
| 5,677,145 | 10/1997 | Ryan | 436/10 |

OTHER PUBLICATIONS

Becton Dickingson Primary Care Diagnostics, QBC E–Z Prep Venous–Blood Tubes: Test Procedures (package insert) (1992).
Becton Dickingson Primary Care Diagnostics, QBC E–Z Prep Capillary–Blood Tubes: Test Procedures (package insert) (1991).
Becton Dickingson & Co., QBC Venous–Blood Tubes (package insert) (1989) (6 pgs.).
Becton Dickingson & Co., QBC Capillary–Blood Tubes (package insert) (1994) (6 pgs.).
Williams, et al., *Hematology* 3d ed., pp. 9–15 and 41 (1984).
Wardlaw et al., *JAMA* 249(5):617–620 (1983).
Wintrobe, *Am. J. Med. Sci.* 185:58–71 (1933).
Rock et al. *JAMA* 249(5):613–616 (1983).
Wintrobe et al., *Clinical Hematology,* 8th edition, pp. 7–19, 205 and 208 (1981).

*Primary Examiner*—Maureen M. Wallenhorst
*Attorney, Agent, or Firm*—Harness, Dickey & Pierce, P.L.C.

[57] ABSTRACT

Quantitative buffy coat (QBC) analysis control compositions are provided which sufficiently mimic whole blood and perform consistently in various QBC systems. The control compositions contain a red blood cell component composed of non-human mammalian red blood cells and a granulocyte component composed of fixed human granulocytes. Methods of making and using the control compositions are also provided.

17 Claims, 3 Drawing Sheets

QUANTITATIVE BUFFY COAT CONTROL COMPOSITION

FIELD OF THE INVENTION

The present invention relates generally to control compositions for quantitative buffy coat analysis, and more particularly to quantitative buffy coat control compositions comprising non-human mammalian red blood cells as the red blood cell component and fixed human granulocytes as the granulocyte component.

BACKGROUND OF THE INVENTION

There are nine parameters that may be evaluated in whole blood, hematocrit, defined as the volume of erythrocytes (RBCs) packed by centrifugation of whole blood given as a percentage of total blood volume; hemoglobin concentration (g Hb/dL blood); mean corpuscular hemoglobin concentration (MCHC), (g Hb/dL RBCs); platelet count; total leukocyte (WBC) count; granulocyte count; lymphocyte/monocyte (ie., nongranulocyte) count; granulocytes given as a percentage of total white blood cell count; and lymphocytes/monocytes given as a percentage of total white blood cell count. The granulocyte, lymphocyte/monocyte, and platelet layers together comprise what is referred to as the "buffy coat."

Quantitative buffy coat (QBC) analysis is routinely performed in clinical laboratories. Quantitative buffy coat analysis (QBCA) techniques generally employ centrifugation of capillary tubes containing whole blood, wherein the whole blood is separated into six distinct layers: packed red cells, red cells, granulocytes, lymphocytes/monocytes, platelets, and plasma. Wardlaw, S. C. et al., *JAMA* 249:617–620 (1993). Based on examination of the tube, the length of the layers is determined and converted into a cell count, thus allowing quantitative measurement of each layer. The length can be measured with a manual reading device ie., a magnification eyepiece and a manual pointing device, or photometrically by an automated optical scanning device which finds the layers by measuring light transmittance and fluorescence along the length of the tube. A series of commonly used QBC instruments are manufactured by Becton-Dickinson.

As the buffy coat layers are very small, the buffy coat is often expanded in the tube for more accurate visual measurement by placing a plastic cylinder, or float, into the tube. The float has a density less than that of RBCs (1.090 g/mL) and greater than that of plasma (1.028 g/mL) and occupies nearly all of the cross-sectional area of the tube. The float therefore rests on the packed RBC layer and axially expands the buffy coat layers. See U.S. Pat. Nos. 4,027,660, 4,082,085, 4,091,659, 4,137,755, 4,141,654 and 4,159,896. To observe the buffy coat regions, a fluorescent stain such as acridine orange (AO) is added to the sample prior to centrifugation. The AO is absorbed by each layer in different degrees, thereby causing the constituent layers to fluoresce to different degrees when exposed to light of the appropriate wavelength.

A typical problem encountered when using the prior art QBC control compositions is the failure of the automated readers to find the bottom of the float at the interface between the packed red cells (deep red) and the red cells (light transparent red), regions 1 and 2, respectively, in FIG. 1). This failure is due to poor light transmittance in region 2, causing the machine to return a "float error." Different machines seem to have different tolerances; a composition that performs satisfactorily on one machine may not perform well on another, even another of the same model.

There are three fundamental criteria which must be met by the red blood cell component of a QBC control. The first is related to the stability of the red cell component over time or the ability of the cells to remain intact at a constant size and not release hemoglobin. The second is related to the ability of the red cell component to transmit a sufficient quantity of light above a wavelength of approximately 580 nm. The third is related to the degree to which the red cell component will adhere to the inner surface of the QBC sample tube. All three criteria are important for successful performance of the control product.

Red cell stability is required for several reasons. First, the hematocrit measured by the QBC system is directly dependent on the quantity of intact red blood cells present; therefore, a stable red cell component is required for this value to exhibit minimal variance overtime. Second, the release of hemoglobin and other cell constituents by unstable red blood cells will alter the physical and chemical nature of the diluent. This in turn can affect the settling of the other components and introduce variation in the other parameters measured by the QBC system. Finally, the release of hemoglobin into the product diluent will lead to an overall decrease of the light transmitted through the QBC tube.

The transmission of light through the red blood cells is important due to the mechanism by which a QBC system operates. In a QBC autoreader, the instrument locates the plastic float within the tube by first measuring the amount of light transmitted at each point along the tube's length. As described above, the instrument searches for the rise in light transmittance corresponding to the bottom of the float and the beginning of the light red cell region, i.e., the interface between regions 1 and 2 as shown in FIG. 1. If the red cells do not transmit sufficient light in region 2, the rise in transmittance will not be large enough for the autoreader to successfully locate the float, causing the machine to return a float error.

The degree of red blood cell adherence in the buffy coat area is important due to the clarity required for proper parameter measurement. A red blood cell component which exhibits a high degree of tube adherence will interfere with the visual definition of the layers in this region. This may result in undesired variance of measured parameters, and leads to a control which is not visually satisfactory. Use of a red cell component which exhibits little or no adherence to the tube surface would result in a product in which the buffy coat layers are visually distinct. Such a product would be expected to generate values which display less variance over time, and would present a clear advantage over controls which exhibit higher degrees of red cell adherence.

In order to meet the stability criterion for the red blood cell component, the cells are generally fixed. However, fixing of the red cells with common fixatives such as glutaraldehyde, results in a lowering of their ability to transmit light. Therefore, a tradeoff exists between increasing red cell stability and maintaining sufficient light transmittance. Examples of this tradeoff can be seen with commercially available controls. In one such control, the red cell component exhibits satisfactory light transmittance in the QBC system; however, the cells are generally unstable, exhibiting visible hemolysis. This suggests that the red cell component is either not fixed or the fixing is at a level that does not markedly increase cell stability. In another commercially available control, the red cell component is reasonably stable; however, the cells transmit light so poorly that the control will not produce acceptable readings in one of the four QBC tube types manufactured. This suggests that the red cell component is fixed at a high level, resulting in a much less transparent red cell region.

Both of the above-described commercially available controls use human red blood cells as the red blood cell component, and in both controls the adherence of the red blood cell component to the inner tube wall is unsatisfactorily high. This results in poor visual definition of the interfaces between layers in the buffy coat region. The visual definition, which is poor initially, tends to deteriorate even further with time, so that within one or two weeks of evaluation, some interfaces become nearly impossible to define.

In addition to the red blood cell component, difficulty has been encountered in obtaining an optimum control which contains other whole blood components or surrogates for these components. Among these components are a granulocyte component, a lymphocyte/monocyte component and a platelet component. The granulocyte layer must be able to achieve the appropriate color and maintain the intensity of the color associated with that of whole blood. The lymphocyte/monocyte component will display a bright fluorescent green color, layer uniformly, and have distinct interfaces. The platelet layer preferably displays all of the qualities of the lymphocyte/monocyte layer, except that it displays an orange color instead of a fluorescent green. Overall, these components should separate into layers similar to those seen in whole blood and should be stable for 45 days in order to serve as acceptable controls.

Another problem encountered in QBCA is the ability of the QBC control to perform satisfactorily in all types of QBC-Series tube types. Generally these tubes include the Standard Venous Blood Tube (SVBT), which uses drawn blood which is already anticoagulated with EDTA; the E-Z Prep Venous Blood Tube (EPVBT) which is the same as the SVBT but with the end closure and float already assembled; the Standard Capillary Blood Tube (SCBT) which uses blood from a finger stick and thus the tube itself must contain the anticoagulant (sodium heparin and dipotassium EDTA); and the E-Z Prep Capillary Blood Tube (EPCBT), which is the same as the SCBT but with the end closure and float already preassembled.

It would thus be desirable to obtain a QBC control which contains red cell, granulocyte, lymphocyte/monocyte and platelet components that separate into distinct components to simulate whole blood. It would also be desirable to provide a QBC control which performs consistently in all commercially available QBC systems and with all commercially available QBC tubes. It would further be desirable to provide a QBC control wherein the red blood cell component is stable. It would also be desirable to provide a QBC control wherein the red blood cell component is sufficiently transparent. It would further be desirable to provide a QBC control wherein the red blood cell component does not adhere to the QBC system tube. It would also be desirable to provide a QBC control wherein the granulocyte component exhibits a sufficiently intense and stable coloration and layers uniformly.

SUMMARY OF THE INVENTION

A QBC control composition which simulates whole blood is provided. The red blood cell component of the control composition of the present invention comprises non-human mammalian red blood cells having a mean corpuscular hemoglobin concentration (MCHC) of less than or equal to about 35 g/dl. It has been found that when these cells are utilized, the control composition is stable, has sufficient light transmittance and does not adhere to the QBC system tube. The QBC control composition of the present invention may also include fixed human granulocytes for the granulocyte component. The fixed granulocytes of the control composition exhibit an intense and stable orange color and layer uniformly with distinct interfaces. In a preferred embodiment, the control composition further comprises fixed human granulocytes for the lymphocyte/monocyte component, polystyrene latex microspheres for the platelet component, and a suspension media. QBC control compositions of the present invention perform consistently in known QBC systems tested, and are usable in all four QBC-Series tube types. Methods for making and using the QBC control compositions of the present invention are also provided herein.

Additional objects, advantages, and features of the present invention will become apparent from the following description and appended claims, taken in conjunction with the accompanying drawings.

BRIEF DESCRIPTION OF THE DRAWINGS

The various advantages of the present invention will become apparent to one skilled in the art by reading the following specification and subjoined claims and by referencing the following drawings in which:

FIG. 3 shows a transmittance scan of fixed rabbit red cells in a standard venous tube.

DETAILED DESCRIPTION OF THE PREFERRED EMBODIMENTS

Figure 1:
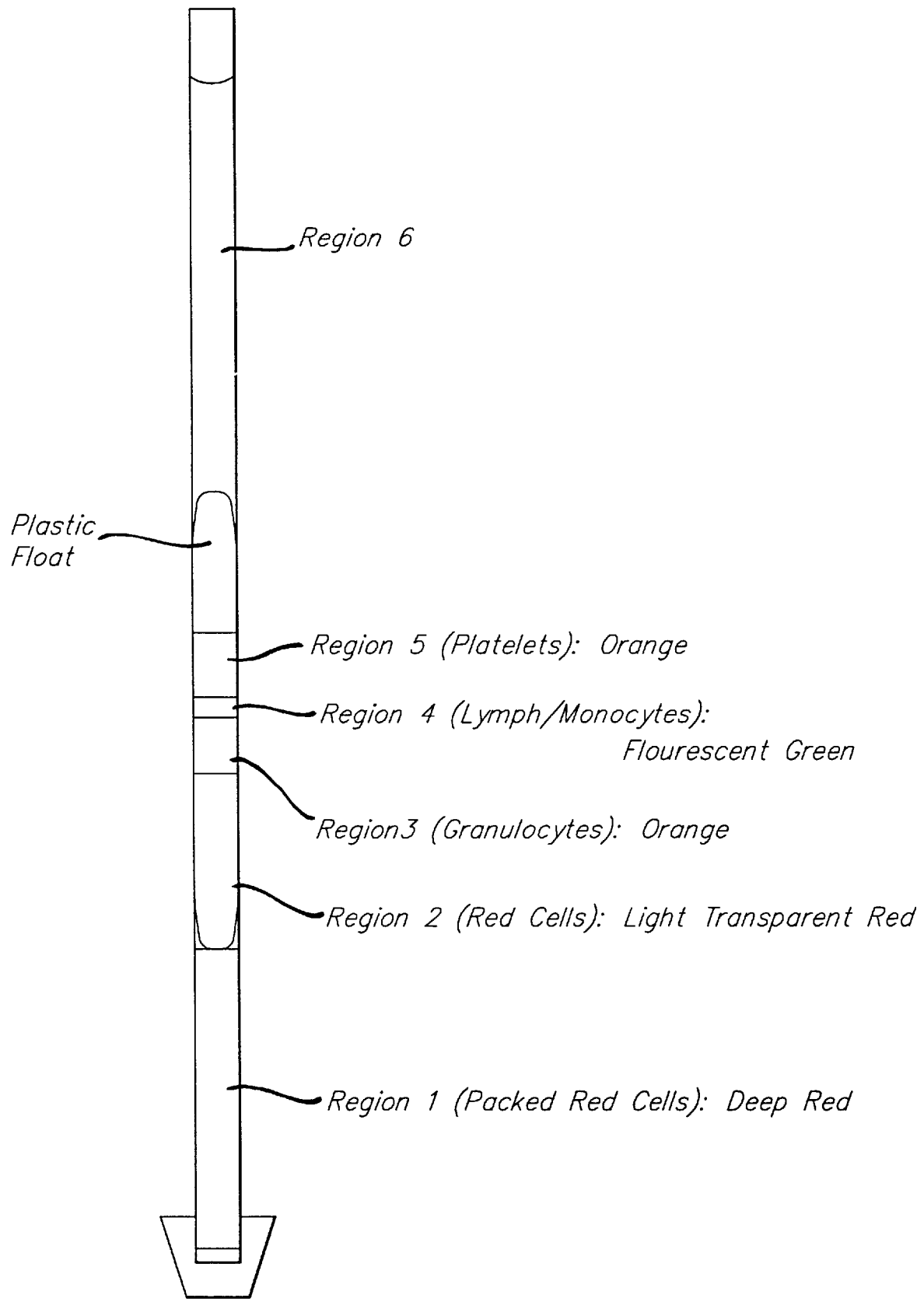
FIG. 1 shows the six distinct layers found in whole blood in a QBC-series tube following high-speed centrifugation.

The QBC control composition of the present invention comprises a stable red blood cell component that is sufficiently transparent to transmit light and does not adhere to the walls of QBC tubes. The QBC control composition of the present invention may also comprise a granulocyte component that exhibits a sufficiently stable and intense coloration and layers uniformly with distinct interfaces. The control compositions of the present invention may further include lymphocyte/monocyte and platelet components that simulate whole blood. The control compositions of the present invention perform consistently in all known QBC systems and with all four known QBC tubes described above.

In one embodiment of the present invention, the red cell component of the QBC control composition is composed of non-human mammalian red blood cells (erythrocytes) which permit acceptable light transmittance, even when the cells are fixed, with no tube residue. Acceptable light transmittance correlates with a mean corpuscular hemoglobin concentration (MCHC) value of less than or equal to about 35 g/dl. Preferred non-human mammalian red blood cells of the present invention include those from rabbit, porcine and horse.

While not wishing to be bound by theory, it is believed that the non-human mammalian blood cells of the present invention permit acceptable light transmittance, even when the cells are fixed, with no tube residue, because they do not adhere to the monoclonal anti-human glycophorin A thought to be present as a dry reagent on the QBC tube inner surface. In whole blood samples, the antibody would be completely solubilized, and any subsequent interaction with red cells would occur in the fluid phase. In prior art controls, however, solubilization of the antibody may be incomplete and adherence of some red cells to residual antibody on the tube surface occurs, causing poor visual definition of the interfaces between layers of the QBC.

In another embodiment, the granulocyte component of the control composition is composed of fixed human granulocytes. In another embodiment, the fixed human granulocytes are stained with ethidium bromide and/or incubated with DMSO.

In yet another embodiment, the control of the present invention further comprises a lymphocyte/monocyte component, platelet component and suspension media (plasma component). In a preferred embodiment, the control composition comprises rabbit red blood cells for the red blood cell component, fixed human granulocytes for the granulocyte component, fixed human granulocytes for the lymphocyte/monocyte component, polystyrene latex microspheres for the platelet component, and a suspension media.

The control compositions of the present invention are stable and provide accurate values in the QBC-Series System for at least 35 days when stored in a closed vial and for at least 7 days when stored in an open vial.

The methods of the present invention generally comprise the use of the QBC control composition of the present invention in a variety of blood analysis applications. As the control compositions of the present invention simulate whole blood, the compositions may be used as controls in the process of quantifying and analyzing the components of unknown whole blood samples. The compositions are particularly useful as a QBC control and may be used with a variety of QBC tubes, in addition to all known QBC systems. Furthermore, it is also in the contemplation of the present invention that these control compositions may be used for proficiency testing.

It will be appreciated that the term "control composition" as used herein means one or more blood components and includes naturally occurring blood components as well as analogues thereof, which when combined or used alone, sufficiently simulate whole blood.

SPECIFIC EXAMPLE 1

The following example describes the preparation of a preferred control composition of the present invention.

8 ml of an aldehyde fixed granulocyte component suspension, 10 ml of a lymphocyte/monocyte component suspension, and 38 ml of a platelet component suspension are added to 944 ml of aldehyde fixed rabbit erythrocytes suspended in an isotonic diluent. When completely mixed, the resulting suspension of components accurately mimics whole blood.

SPECIFIC EXAMPLE 2

The following example describes in greater detail the red blood cell, granulocyte, lymphocyte/monocyte and platelet components and suspension media of the control compositions of the present invention.

A. Red Blood Cells

Generally, for QBC systems, a control composition having a red blood cell component which exhibits no tube residue, maximal light transmittance, good hematocrit stability, and minimal hemolysis, is desired. The present invention provides non-human mammalian red blood cells having an MCHC of less than or equal to about 35 g/dl, as a source of red blood cells. Preferred cells are from rabbit, porcine and horse. The following table shows the results of testing of different cell sources:

| RBC Source | MCHC (g/dL) | Autoreader Light Transmittance |
| --- | --- | --- |
| Rabbit | 33.3 | Very good |
| Porcine | 33.1 | Very good |
| Horse | 34.8 | Good |
| Goat | 36.7 | Poor |
| Bovine | 39.0 | Poor |
| Sheep | 44.5 | Very poor |

Tube Residue

As stated above, there is no visible tube residue when the red blood cells of the present invention are used as the red cell component in the control composition. The buffy coat layers appear very clear and the interfaces are sharp and easily defined.

Transmittance

Figure 2:
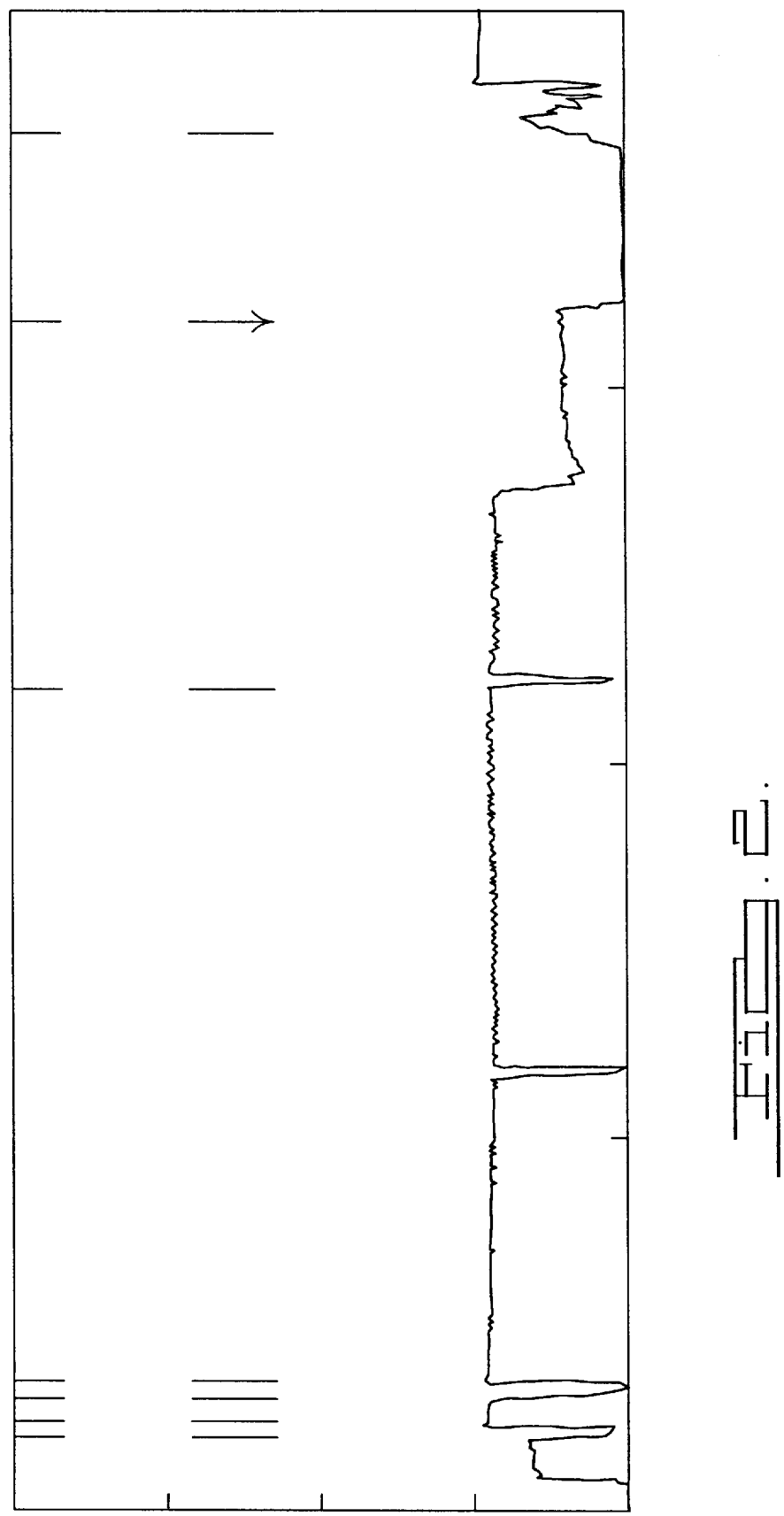
FIG. 2 shows a transmittance scan of unfixed rabbit red cells in a standard venous tube.
Figure 7:
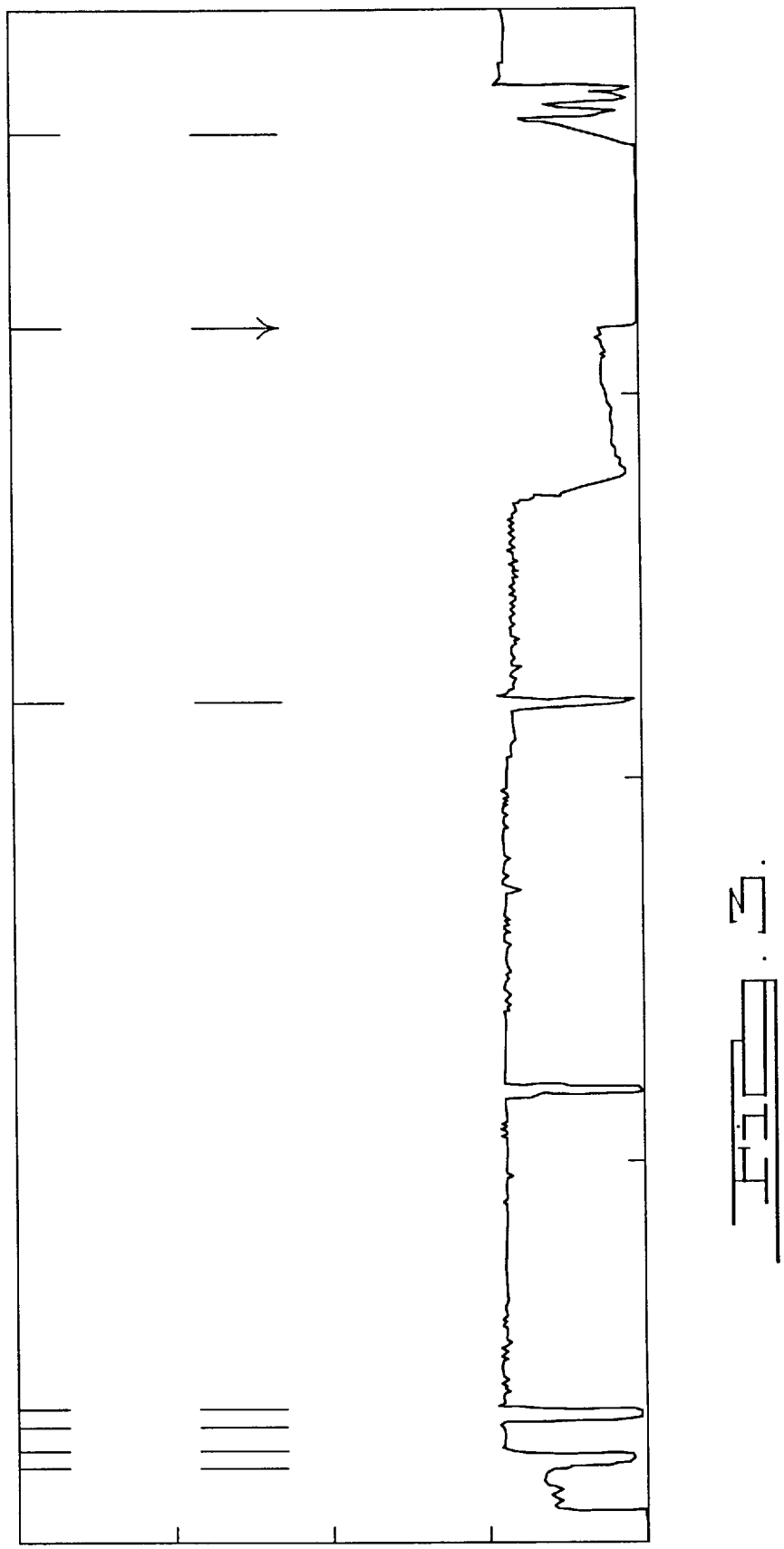

When thinned red blood cells of the present invention are used as the red cell component, the amount of light transmitted through the float region is comparable to that seen with human erythrocytes. FIGS. 2 and 3 show transmittance scans of rabbit red cells which were unfixed and fixed with glutaraldehyde at a concentration of 0.006%, respectively, in a cell suspending solution having the following formula:

| Component | Range g/l | Preferred Concentration g/l |
| --- | --- | --- |
| PEG 20,000 (Polyethylene Glycol) | 1.00–6.00 | 3.00 |
| EDTA disodium salt | 5.00–25.00 | 16.75 |
| Mg Gluconate | 5.00–15.00 | 9.33 |
| Sodium Phosphate | 2.00–10.00 | 6.39 |
| Methyl Paraben | 0.20–0.90 | 0.40 |
| Sodium Hydroxide | (to correct pH) | 2.04 |
| Adenosine | 0.00–1.00 | 0.25 |
| Inosine | 0.00–1.00 | 0.25 |
| Neomycin Sulfate | 0.10–1.00 | 0.40 |
| Chloramphenicol | 0.00–1.00 | 0.15 |
| Distilled Water |  | To Volume |

As is the case with human cells, a slight decrease in the transmittance rise is apparent when comparing fixed versus unfixed cells; however, the transmittance in Region 2 is still far enough above the baseline that the transmittance is sufficient.

Stability

Studies of the hematocrit stability of glutaraldehyde-fixed rabbit red blood cells indicate that following a post-fix equilibrium time of approximately two weeks, the cells exhibit an acceptable level of stability over a 60 day period.

Hemolysis

Hemolysis studies have indicated that glutaraldehyde-fixed rabbit red blood cells do not exhibit marked hemolysis over a 60 day period.

Summary

The red blood cells of the present invention transmit light at a level comparable to human red cells, yet do not exhibit the tube residue characteristic of human cells. In addition, they are stable with regard to hematocrit and exhibit low hemolysis.

B. Granulocyte Component

Generally, for QBC systems, a control composition having a granulocyte component which over at least a 45 day period exhibits an intense and stable orange color, layers uniformly in sample tubes, and has distinct interfaces with the red cell component and the lymphocyte/monocyte component, is desired. Fixed human granulocytes were found to possess optimum qualities for the control of the present invention. The human granulocytes may be fixed by methods and fixation agents known to those skilled in the art. In a preferred embodiment, the human granulocytes are fixed with formaldehyde and glutaraldehyde. More specifically, the fixed human granulocytes may be prepared by the following method (see also, U.S. Pat. No. 5,270,208, column 4, lines 15–28): concentrated white blood cell packs from commercial blood banks are washed in ammonium chloride-Tris solution to remove the red blood cells; the cells are further washed with a buffered solution that permits osmotic swelling of the white blood cells (PEG 20,000, EDTA, osmo 200); and, the cells are fixed by mixing 1 part cell suspension with 2 parts of a solution containing 7.4% formaldehyde and 0.125% glutaraldehyde.

Color/Intensity

A granulocyte component which appears intensely orange was obtained when fixed human granulocytes were stained at 40° C. using an aqueous solution of ethidium bromide (100 mg % in water). Other dyes, including Acridine Orange, FITC, Hoechst stain 33258, D-291, and propidium iodide, did not produce the desired orange color when viewed in the QBC System.

In order to prevent loss of ethidium bromide from cells, DMSO was used to shrink the stained fixed cells. A procedure was developed involving incubation of stained fixed cells with a mixture of DMSO and the cell suspending solution described in the above tables (90% DMSO and 10% cell suspending solution) at 40° C. for 24 hours. Several batches of fixed granulocytes have been processed according to this procedure; in each case the resulting granulocyte component exhibited an extremely intense orange color in the QBC System that did not significantly diminish over time. Without wishing to be bound by theory, it is believed that by shrinking the fixed cells with DMSO, the fluorescence intensity per unit volume of cells increases, resulting in enhanced color intensity in the QBC System and the average cell membrane pore size is reduced as the cell shrinks, resulting in hindered transport of dye out of the cell, and thus better long-term retention of color.

Size/Density

Fixed human granulocytes that have been stained according to the aqueous ethidium bromide procedure exhibit a fuzzy interface with the lymphocyte/monocyte layer prior to incubation with DMSO. These interfaces become very distinct following incubation of the stained fixed cells with the DMSO/Para 8® Final mixture. It is believed that by shrinking the fixed cells their size and/or density is being adjusted in such a way as to further distinguish them from the lymphocyte/monocyte component. Several batches of fixed granulocytes have been processed according to this procedure and have resulted in consistent observations.

C. Lymphocyte/Monocyte Component

Generally, for QBC systems, a control composition having a lymphocyte/monocyte component which over at least a 45 day period exhibits a bright fluorescent green color, layer uniformly in sample tubes, and has distinct interfaces with the granulocyte component and the platelet component, is desired.

It was found that human granulocytes are a good source for the lymphocyte/monocyte component. The human granulocytes are fixed preferably in two steps. The first is with formaldehyde at a concentration of 10% and the second is with formaldehyde at a concentration of 5%. It will be appreciated to those skilled in the art that other fixing agents and methods may likewise be employed.

In a preferred embodiment, the following method is employed to prepare the human granulocytes (see also, U.S. Pat. No. 5,270,209, column 4, lines 15–28): concentrated white blood cell packs from commercial blood banks are washed in ammonium chloride-Tris solution to remove the red blood cells; the cells are fixed in a hypotonic buffered solution containing 10% formaldehyde (phosphate buffered saline, Osmolarity=200 mosM); and, the cells are washed into buffered solution.

The size and density of the fixed cells can be adjusted in order to achieve sufficient layering with clear interfaces by incubating at 40° C. up to 4 days. This procedure has been repeated with consistent results.

D. Platelet Component

Generally, for QBC systems, a control composition having a platelet component which over at least a 45 day period exhibits an orange color, layers uniformly in sample tubes, and has distinct interfaces with the lymphocyte/monocyte component and the plasma column above the layer, is desired.

An orange layer is observed in the QBC System when polystyrene latex microspheres in the range of 1.5 to 2.5 $\mu$m diameter are used (Polysciences, Inc., Warrington, Pa.). The orange color is most likely a result of the uptake of Acridine Orange within the sample tube by the latex particles. Dye which associates with the latex will fluoresce an orange color, thus causing the latex layer to appear orange in the QBC System. The 2.0 $\mu$m diameter Polysciences latex is preferred.

E. Suspension Media

The suspension media of the present invention is generally an isotonic aqueous suspension media. In a preferred embodiment, the suspension media comprises an aqueous solution comprising the following components at their corresponding concentrations: PEG 20,000, 3.0 g/l; EDTA, disodium salt, 7.04 g/l; magnesium gluconate, 8.0 g/l; sodium phosphate, dibasic, 2.68 g/dl; methyl paraben, 0.4 g/l; sodium hydroxide, 1.13 g/l; adenosine, 0.25 g/l; inosine, 0.25 g/l; neomycin sulfate, 0.4 g/l; and chloramphenicol, 0.3 g/l; Hexadimethrine bromide (Polybrene®), 0.1 g/l. The pH and osmolarity are adjusted to 7.0 and 315, respectively.

A cationic substance may also be added to the media including, but not limited to, polylysine, protamine, polybrene (Hexadimethrine bromide) and mixtures thereof. In particular, the cationic substance may be employed when standard or EZ Prep Capillary tubes are used because these tubes contain sodium heparin, a strongly anionic substance that prevents blood clotting and will interfere with the sedimentation of red blood cells due to their charge.

SPECIFIC EXAMPLE 3

Analysis

The following is a description of the characteristics that are generally analyzed in evaluating QBC control compositions.

Tube Residue

Tube residue refers to the degree to which red blood cells will adhere to the sample tube wall. To maximize clarity of the layers in the buffy coat region, a superior control will have a red blood cell component which exhibits no tube residue.

Transmittance

Transmittance refers to the amount of light which passes through the red blood cell layer designated as region 2 in FIG. 1. As discussed above, because the autoreader uses light transmittance to physically locate the plastic float within the sample tube, the amount of light transmitted by this red blood cell layer is crucial. A superior control will therefore have a red blood cell component which exhibits maximal light transmittance in this region.

Stability

Stability refers to low variation in measured parameter values over a 45 day period. A superior control will exhibit high stability over this time scale.

Hemolysis

Hemolysis refers to visible darkening of the product diluent as hemoglobin is released from aged red cells. A superior product will contain a red blood cell component that exhibits hemolysis below a Level 1 (on a semi-quantitative scale from 0 to 4) over at least a 45 day period.

Color/Intensity

Color/Intensity refers to the colors and intensities of the respective component layers when viewed in the QBC system. A superior product will consist of components which exhibit the same or nearly the same colors as those seen in whole blood specimens, and will maintain the intensities of these colors over at least a 45 day period.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

All patents and other publications cited herein are expressly incorporated by reference.

We claim:

1. A quantitative buffy coat analysis control composition comprising a red blood cell component wherein the red blood cell component comprises non-human mammalian red blood cells having a mean corpuscular hemoglobin concentration of less than or equal to about 35 g/dl.

2. The composition of claim 1, wherein the non-human mammalian red blood cells are selected from the group consisting of rabbit, porcine and horse red blood cells, and mixtures thereof.

3. The composition of claim 2, wherein the non-human mammalian red blood cells are rabbit red blood cells.

4. The composition of claim 1, further comprising:

a) a granulocyte component;

b) a lymphocyte/monocyte component; and c) a platelet component.

5. The composition of claim 4, wherein the granulocyte component comprises fixed human granulocytes.

6. The composition of claim 4, wherein the lymphocyte/monocyte component comprises fixed human granulocytes.

7. The composition of claim 4, wherein the platelet component comprises polystyrene latex microspheres.

8. A method of using the composition of claim 4 as a control in the analysis of whole blood.

9. A method of using the composition of claim 1 as a control in the analysis of whole blood.

10. A method of making a control composition for quantitative buffy coat analysis, comprising the step of mixing non-human mammalian red blood cells having a mean corpuscular hemoglobin concentration of less than or equal to 35 g/dl with a granulocyte component, a lymphocyte/monocyte component and a platelet component in an isotonic aqueous suspension medium.

11. The method of claim 10, wherein the composition comprises fixed human granulocytes as the granulocyte component.

12. The method of claim 10, wherein the non-human mammalian red blood cells are selected from the group consisting of rabbit, porcine and horse red blood cells, and mixtures thereof.

13. The method of claim 12, wherein the non-human mammalian red blood cells are rabbit red blood cells.

14. A method of determining the accuracy of a quantitative buffy coat analysis system comprising the steps of:

a) passing a blood cell control composition through the analysis system to provide a control value wherein the blood cell control composition has an assayed value and comprises non-human mammalian red blood cells having a mean corpuscular hemoglobin concentration of less than or equal to about 35 g/dl, a granulocyte component, a lymphocyte/monocyte component and a platelet component, suspended in an isotonic aqueous suspension medium; and b) comparing the control value of step a) with the assayed value of the control composition.

15. The method of claim 14, wherein the control composition further comprises fixed human granulocytes as the granulocyte component.

16. The method of claim 14, wherein the non-human mammalian red blood cells are selected from the group consisting of rabbit, porcine and horse red blood cells, and mixtures thereof.

17. The method of claim 16, wherein the non-human mammalian red blood cells are rabbit red blood cells.

* * * * *